United States Patent [19]

Gottlieb

[11] Patent Number: 4,778,750

[45] Date of Patent: Oct. 18, 1988

[54] DIAGNOSTIC METHODS FOR IMMUNE FUNCTION

[75] Inventor: A. Arthur Gottlieb, New Orleans, La.

[73] Assignee: Imreg, Inc., New Orleans, La.

[21] Appl. No.: 830,728

[22] Filed: Feb. 19, 1986

[51] Int. Cl.[4] .................. G01N 33/50; G01N 33/535; G01N 33/569; G01N 33/577

[52] U.S. Cl. ............................................ 435/5; 435/7; 435/29; 436/513; 436/548; 530/351

[58] Field of Search .................. 436/513, 519, 548; 435/5, 7, 28; 530/351

[56] References Cited

U.S. PATENT DOCUMENTS

| | | | |
|---|---|---|---|
| 4,426,454 | 1/1984 | Aoki | 436/504 |
| 4,436,824 | 3/1984 | Bishop | 436/519 X |
| 4,468,379 | 8/1984 | Gottlieb | 424/101 |
| 4,610,878 | 9/1986 | Wilson | 435/4 X |
| 4,614,722 | 9/1986 | Pasula | 436/513 X |

OTHER PUBLICATIONS

D'Andrea, A. D., J. Clin. Microbiol., 23(5), 911-915 (1986).

*Primary Examiner*—Sidney Marantz
*Attorney, Agent, or Firm*—Richard H. Stern

[57] ABSTRACT

A diagnostic test is described for the assay of human and animal immune system response, in vitro. The test measures production in a peripheral blood lymphocyte population of a material that is an index of mitogen-induced immune response. Adaptations of the test are provided for the titration of amplifier dosage, and for a determination whether amplifier treatment is warranted for immunodeficient patients such as those with AIDS or ARC.

25 Claims, No Drawings

DIAGNOSTIC METHODS FOR IMMUNE FUNCTION

BACKGROUND OF THE INVENTION

1. Field of the Invention

The present invention relates to means of determining the immune function of a human being or animal. In a number of diseases or other pathological conditions, the immune system response of the human or animal subject is depressed. As a result the subject becomes more susceptible to opportunistic infections, malignancies, or other pathological conditions against which a normal immune system would have protected the subject. Among the pathological conditions that depress the immune system are Acquired Immune Deficiency Syndrome (AIDS) and AIDS-related complex (ARC). Chemotherapy and aging are also associated with immune deficiency.

In other conditions or circumstances, immune system response may be excessive relative to what is medically desired. For example, lupus, multiple sclerosis, arthritis, and diabetes may involve excessive immune system response. When organ transplants are required, it is often medically desirable to lower the subject's immune system response to avoid rejection of the organ transplant.

Convenient, inexpensive, in vitro diagnostic tests for diagnosing impairment or level of immune function are presently unavailable. In particular, such quantitative tests are unavailable. However, such quantitative tests would be very useful in therapeutic regimes, for several purposes. Such tests would be helpful in assessing the remaining immune function of a person whose immune system has been damaged, such as by chemotherapy or AIDS, as a diagnostic indicating the need for or feasibility of other treatment and the appropriate extent thereof. Such tests are also helpful in titrating to an acceptable amount the dosage of substances known to impair immune function, in titrating the dosage of substances deliberately administered to modify (suppress or amplify) immune function, and qualitatively in determining whether a person or animal suffers from a condition impairing immune function.

2. Other Background

The inventor has discovered that lymphocyte dialysates contain immunodulators, which are materials or substances having therapeutic utility, as described in detail in U.S. Pat. No. 4,468,379. The '379 patent discloses a process for extracting such substances and methods of using them. Other processes are disclosed in pending U.S. application Ser. No. 643,724. In general, immunomodulators have the property of modulating the response of a subject's immune system to antigens to which the subject's system has been previously exposed. Amplifier immunomodulators, or amplifiers (or immunoamplifiers), amplify or accelerate immune response. Suppressor immunomodulators, or suppressors, suppress immune response.

Transfer factors have also been reported to have been derived from lymphocyte dialysates or leukocyte extracts. Immunomodulators have been distinguished from transfer factors, in that immunomodulators are not specific to particular antigens (whereas transfer factors are) and immunomodulators generically affect immune response to any antigen to which the subject has been exposed (whereas transfer factors do not). Transfer factors are reported to transfer an immune response only to antigens to which the donor was exposed, and to do so irrespective of whether the subject to which the factor is administered ever had previously been exposed to such antigens.

The inventor's '379 patent discloses procedures in which test subjects are exposed to antigens, with and without dosages of immunomodulators, and the immune responses are compared. The pending '724 application discloses similar information. The '724 application also discloses the treatment of AIDS and ARC patients with amplifiers to restore their immune function, in whole or in part, so long as enough residual immune function remains to permit the treatment to be effective. Abstracts published in April 1984 and April 1985, A. Arthur Gottlieb and J. L. Farmer, "Reconstitution of T cell function in AIDS patients by use of leukocyte-derived endogenous immunomodulators," Clinical Research 32: 504A and 33: 557, also describe the foregoing AIDS treatments in general terms; the abstracts also state that the authors observed that the patients demonstrated no or low responsiveness to PHA (phytohemagglutinin, a substance to which lymphocytes of healthy subjects respond) before therapy, while after therapy they displayed enhancement of their PHA responsiveness with associated increases in production of interleukin-2, and enhancement of delayed type hypersensitivity reaction to tetanus toxoid in several patients.

Other, as yet unpublished, work of the inventor, described in a co-pending application, "Tripeptides affecting immune response," Ser. No. 813,586 filed Dec. 26, 1985 (hereinafter referred to at times as the Tripeptides patent application), indicates that immunomodulatory effects similar to those obtained with the foregoing immunomodulators may be obtained by use of the tripeptide Tyr-Gly-Gly (TGG) and related molecules.

SUMMARY OF THE PRESENT INVENTION

The present invention is an in vitro test method for determining the magnitude of immune response function of an animal or human subject by assaying the ability of the subject's leukocytes to produce materials associated with the operation of the immune system. In particular, the invention permits the measurement of "immune reserve" (i.e., remaining immune capacity) in a subject with an impaired immune system (i.e., a subject whose immune response to antigen is subnormal).

The procedure of this invention begins with isolation, by known procedures, or peripheral blood lymphocytes (PBLs, also referred to as peripheral blood mononuclear cells). The PBLs are exposed in vitro to mitogen or antigen. Then the production of interleukin-2 (IL-2) in response to mitogen is assayed. (The preferred embodiment uses the mitogen phytochemoagglutinin, PHA, but pokeweed mitogen, PWM, has also been used successfully, and the procedure is not restricted to any particular mitogen. As indicated above, tetanus toxoid is another usable stimulus, and other antigens may be used that provoke an immune system response. Moreover, while the preferred embodiment is based on assaying the production of IL-2, other immune response products may be used for the assay, such as gamma-interferon and generation of cytotoxic lymphocytes, and the procedure is not restricted to any particular such index.)

In the case of a subject with an impaired immune system, the subject's mitogen-induced IL-2 production in vitro is substantially lessened, in the absence of addition of immunoamplifiers. However, the mitogen-induced production of IL-2 is increased substantially, in the case of such subjects having residual or remaining immune response, by the addition of reagents containing amplifiers. On the other hand, when such subjects have very little or no immune reserve, such reagents have no significant effect in increasing IL-2 production. The ability of such reagents to increase mitogen-induced IL-2 production in vitro thus provides a convenient means to assay immune reserve, and thus assay the level to which the subject's immune function can be raised by treatment.

DETAILED DESCRIPTION OF PREFERRED EMBODIMENT

The procedure of this invention provides a means of assaying immune function, specifically immune reserve. The basic steps are extraction of blood from the animal or human subject, preparation of purified peripheral blood mononuclear cell (PBL) populations, addition of mitogen to the purified PBL populations (with and without amplifier reagent), and assay of IL-2 production.

I. Isolation and fractionation of peripheral lymphocytes

Venous blood was extracted from normal subjects and from patients with AIDS or ARC. An appropriate sample is approximately 20 to 25 ml/patient.

EXAMPLE 1

Isolation of PBLs

Peripheral blood mononuclear cells (PBLs) were obtained from heparinized blood samples, by density gradient centrifugation on Lymphocyte Separation Medium (LSM) (Litton Bionetics, Kensington, MD). The cells of interest are those found at the interface. The cells were washed 3× in RPMI 1640 medium containing 25 mM HEPES (GIBCO, Grand Island, NY).

II. Amplifier Bioassay

A. Mitogen exposure and culture

Preparations of Amplifier Beta of the '724 application, Example 7 (the product concentration being that amount of amplifier derived from $400 \times 10^6$ buffy coat leukocytes, in each 1 ml of aqueous saline) were diluted with aqueous saline to provide the following reagents:

| Reagent | A | B | C |
|---------|-----|------|------|
| Dilution, 1: | 500 | 1000 | 2000. |

Reagent D was prepared, also, consisting of sterile normal saline.

The dilutions of Reagents A, B, and C correspond approximately to the amount of Amplifier Beta recovered by the inventor's process (of the '724 patent application) from 800,000, 400,000, and 200,000 leukocytes, respectively. The inventor has determined empirically that those three dilutions, in the procedure of Example 2, are satisfactory to accomplish the kind of assay described herein. Those skilled in the art will appreciate, however, by examining the data tabulated below, that other, as well as more or fewer, dilutions of this type may be selected to accomplish the kind of results one desires, using this disclosure as a guide. (For example, more closely spaced dilutions—such as 1:200, 300, 400, 500, 600, 800, 1000, 1200, 1500, 1800, 2000, 2400, 3000—will more precisely measure the maximum IL-2 production achievable. That procedure, however, will also (1) require extraction of more blood from the test subject and (2) be more laborious and costly.) Accordingly, the inventor does not consider the invention to be limited to the particular quantities of reagent specified in the examples. Rather, the invention includes the use of such other proportions, as well, that the disclosure would teach a skilled person to utilize with necessary experimentation as suggested by the disclosure.

EXAMPLE 2

Preparation of Mitogen-containing Culture

PBLs of Example 1 are obtained from test subjects (here, as tabulated below, five normal test subjects and seven AIDS/ARC patients). The PBLs are resuspended to $1 \times 10^6$/ml in RPMI 1640 medium containing 25 mM HEPES, supplemented with 10% FCS, 100 µg/ml streptomycin, and 100 U/ml penicillin. (The lower case letter u is used hereinafter to represent micro, as in ug or ul, for micrograms and microliters, respectively; the upper case letter U hereinafter represents Units.)

At least four 200 ul aliquots (and preferably a multiple of four, such as five sets of four, or 20, to permit subsequent pooling of aliquots for averaging purposes) of each test subject's resuspension are dispensed into the wells of 96-well microtiter plates (Falcon Labs #3072). To each of the four sets of each test subject's aliquots was added, respectively, 20 ul of Reagent A, B, C, or D. In addition, a suitable amount of PHA mitogen (Wellcome Reagents HA 16) is added to each well, in a volume of 20 ul/well.

The resulting materials are incubated at 37° C., 5% $CO_2$, for 24 hours. Replicate supernatants are harvested (pooled as appropriate), and frozen until assayed.

B. IL-2 assay

IL-2 level was determined by measuring the incorporation of radioactively tagged thydiminine, 3H-TdR (New England Nuclear, Boston, Mass.), into the IL-2 dependent cell line CTLL-2 (American Type Culture Collection, Rockville, Md.), using a novel method that the inventor developed for this purpose, and departing in various respects, from that of Gillis et al., "T cell growth factor: parameters of production and a quantitative microassay for activity," 120 J. Immunology 2027 (1978).

EXAMPLE 3

Amplifier Assay Procedure

Log phase CTLL-2 cells are resuspended to $10^5$/ml in an enriched assay medium (RPMI 1640, 25 mM HEPES supplemented with 15%-FCS, 50 uM 2-mercaptoethanol, 2 mM L-glutamine, 100 U/ml penicillin, 100 ug/ml streptomycin). 100 ul aliquots are distributed to the wells of 96-well flat bottom microtiter plates.

The frozen supernatants of Example 2 are thawed. Serial dilutions are prepared, with aqueous saline, to provide undiluted, 50%, and 25% samples, respectively, which are distributed to the wells for culturing.

The cultures are incubated at 37° C., 5% $CO_2$, for 24 hours; 1 uCi/well 3H-TdR (New England Nuclear, Boston, Mass.) is added for the terminal 5 hours of incubation. The cultures are harvested on filter discs using a MASH II unit by standard procedures, including washing, which are well known in the art.

The filter discs (containing the cells) are subjected to liquid scintillation counting to determine the amount of 3H Thymidine incorporated. Counts per minute (cpm) are recorded and the data was analyzed as stated below. In the absence of IL-2, CTLL-2 cells in this system incorporate less than 500 cpm/culture, with maximal incorporation running to approximately 30,000 to 40,000 cpm/culture.

An alternative assay method may be used in which thymidine is tagged with another measuring means, such as a fluorescent dye or fluorescent antibody.

C. Reference preparation

A standard IL-2 preparation was made for relative activity comparison, using 3H-Tdr. It was prepared by incubating $10^6$/ml rat splenocytes with 10 ug/ml Con A (Sigma Chem. Co., St. Louis, Concanavalin A, No. C-2010, Type IV) for 24 hours. This preparation was defined as 10 U/ml IL-2. Therefore, the following formula was established for U/ml IL-2:

$$U/ml\ IL\text{-}2 = \frac{10 \times \text{dilution of experimental sample for 50\% maximum cpm}}{\text{dilution of rat standard for 50\% maximum cpm}}.$$

Under these assay conditions, 50% of maximal 3H-TdR incorporation by CTTL-2 cells represents 0.7 U/ml of the reference human IL-2 preparation supplied by the U.S. National Cancer Institute's Biological Response Modifiers Program.

Normal subjects' PBLs generally yield from 0.9 to 7.0 U/ml IL-2 using 1 ug/ml PHA in the cultures, which is approximately an optimal PHA dosage. (Note: 1 ug/ml PHA is equivalent to 20 ul/well, using the procedure of Example 2.) Most such subjects fall between 1 and 3 U/ml.

III. Results of amplifier assays

The following Tables show representative results of the procedure described in Examples 2 and 3, when PHA was used as a mitogen to stimulate IL-2 production. Increased levels of IL-2 resulted when Amplifier Beta was also added. In control studies, use of Amplifier Beta did not result in IL-2 production in the absence of mitogen. It was also observed that high concentrations of amplifier may cause a paradoxical or suppressive effect, which vanishes when the amplifier is diluted somewhat.

TABLE 1

Modulation of IL-2 Production by Beta, PHA-stimulated Normal PBLs

| | U/ml IL-2 produced in response to 1 ug/ml PHA + Reagent | | | |
|---|---|---|---|---|
| | Reagent A | Reagent B | Reagent C | Reagent D |
| Normal #1 | 2.38 | 2.29 | 2.14 | 1.62 |
| Normal #2 | 11.8 | 11.8 | 13.0 | 11.6 |
| Normal #3 | N/A | 10.4 | 16.8 | 8.3 |

TABLE 2

Modulation of IL-2 Production by Beta, PHA-stimulated AIDS/ARC Patients

| | U/ml IL-2 produced in response to 1 ug/ml PHA + Reagent | | | |
|---|---|---|---|---|
| | Reagent A | Reagent B | Reagent C | Reagent D |
| ARC #1 | 3.71 | 3.71 | 3.84 | 2.08 |
| ARC #2 | 0.08 | 0.09 | 0.21 | 0.06 |
| ARC #3 | 0.55 | 1.37 | 0.60 | 0.28 |
| AIDS #1 | 1.58 | 1.13 | 1.11 | 0.86 |
| AIDS #2 | 1.8 | 0.62 | 0.71 | 0.45 |

These tables indicate varying ratios of IL-2 production in response to PHA alone (Reagent D) and in response to PHA plus Amplifier Beta; for different subjects the concentration of PHA plus amplifier producing maximum IL-2 production relative to IL-2 production under stimulation with PHA alone was different. The ratio between the two productions was calculated from each concentration of Amplifier used (i.e., the different Reagents A, B, and C) and each subject, using the Reagent D IL-2 productions as denominators. The maximum one of such ratios is tabulated in Table 3 for each particular subject. (Ratios based on a zero or near-zero Reagent D production as denominator are not shown, since such a ratio (infinity) is essentially meaningless). Also shown in Table 3 is the maximum IL-2 production for each person, which occured always in the case of 1.0 ug/ml PHA plus whatever was the optimal Beta dilution. Both ratio and absolute production (U/ml) may be used as assay indicators. Because the normal range tends to be approximately 1.0 U/ml, however, it is believed more simple and useful to utilize the U/ml figure.

TABLE 3

Ratio of IL-2 Production in Normal and AIDS/ARC PBLs Resulting from PHA-stimulation and from PHA + Beta-stimulation

| Subject | Highest IL-2 Ratio (PHA + Beta)/PHA | Highest IL-2 Production |
|---|---|---|
| Normal #1 | 1.47 (ratio) | 2.38 U/ml |
| Normal #2 | 1.12 | 13.0 |
| Normal #3 | 2.02 | 16.8 |
| ARC #1 | 1.85 | 3.84 |
| ARC #2 | 3.50 | 0.21 |
| ARC #3 | 4.89 | 1.37 |
| AIDS #1 | 1.84 | 1.58 |
| AIDS #2 | 4.0 | 1.8 |

In all cases, Amplifier Beta increased the in vitro measurement of immune response significantly. In the case of PBLs from normal persons, the IL-2 production stimulated by PHA+Beta was almost always a maximum of twice or more the production that PHA alone stimulated. In PBLs of ARC/AIDS patients, the same ratio ranged from somewhat below a factor of 2 in some cases to much greater improvements in half or more of the sample. In PBLs of most normal persons, the maximum IL-2 production that could be elicited was greater than the maximum production that could be elicited for PBLs of ARC/AIDS patients. In general, then, it may be concluded that Amplifier Beta causes a relatively greater percentage of increase on ARC/AIDS patient PBLs' IL-2 production than it does on normal person PBLs' production, but it usually cannot bring AIDS/ARC patient PBLs' amount of IL-2 production up to the same levels as normal person PBLs' maximum amount of production.

IV. Use of TGG in Assaying Amplifier Function

The inventor has discovered, and has disclosed in the previously cited co-pending Tripeptides patent application, that the tripeptide TGG (Tyr-Gly-Gly) and related products have an immunomodulatory effect similar to that of Amplifier Beta and other immunoamplifiers. He hypothesizes that TGG is an important constituent of Amplifier Beta and similar amplifiers. That in turn suggested the substitution of TGG for amplifier in the foregoing assay procedure. While TGG may not have all the properties of the amplifiers disclosed in the inventor's cited patent and application, nonetheless it is considerably cheaper and easier to obtain. Therefore, a test based on TGG has significant economic advantages even if its accuracy as an index of immune function may not necessarily be as good as that of such amplifiers.

Preparations of TGG were prepared, to repeat the procedure described above. TGG, purified in accordance with the procedures of the cited co-pending Tripeptides patent application, was prepared to various dilutions. The starting dilution was 1:1000, which is approximately $3 \times 10^{-10}$ M. A preparation of 1 ug/ml PHA was also prepared and used as before.

EXAMPLE 4

TGG tests

The procedures of Examples 2 and 3 are repeated with two normal test subjects, using TGG preparations instead of Preparations Amplifier Beta preparations. In Tables 4, the assay results are tabulated, as in Tables 1 and 3.

TABLE 4

IL-2 Production in Normal PBLs in Response to PHA and TGG

| Dilution of TGG | IL-2 production | Maximum ratio over control |
|---|---|---|
| Subject #1 | | |
| control | 0.69 | 2.55 |
| 1:1000 | 1.0 | |
| 1:2000 | 0.93 | |
| 1:4000 | 1.41 | |
| 1:8000 | 1.76 | |
| 1:10,000 | 1.6 | |
| Subject #2 | | |
| control | 0.90 | 1.53 |
| 1:4000 | 0.99 | |
| 1:8000 | 1.06 | |
| 1:16,000 | 1.28 | |
| 1:32,000 | 1.38 | |

The data is generally consistent with that for Amplifier Beta. It indicates a normal PBL range of IL-2 production that can be approximately doubled by TGG, in vitro.

V. Therapeutic utilization of test

It is clear from the preceding tables that Amplifier Beta and TGG have the ability to enhance the ability of lymphocytes from immunodeficient patients to produce IL-2 in response to a suitable stimulus, such as a mitogen. The increment in IL-2 production is a reflection of the potential ability of the patient's cells to release IL-2 and therefore is a measure of the potential capacity of such cells to produce IL-2. Because the patient's cells do not produce so great a quantity of IL-2 without Beta or TGG, even when the cells are given maximal mitogen stimulation, the increment in IL-2 production is a measure of the reserve (but previously unutilized) capacity of the cells to produce IL-2, and by inference to produce other immunoregulatory materials.

The experimental data discussed above leads to the provision of diagnostic methods, and compositions for performing such methods (i.e., kits). As indicated earlier, the invention disclosed herein provides in vitro means of assaying human and animal immune response in a number of circumstances where such assays are useful for medical and veterinary purposes. (As indicated in the '724 application, methods applicable to human subjects may be adapted to animal subjects to accomplish the same purposes.) The following examples are intended to illustrate the use of the assay method described above. In these examples, the following terminology is at times used: "immune reserve" refers to the maximal immune response caused by mitogen plus amplifier (such as by use of Reagents A, B, or C, whichever produces a maximal response); "base immune response" refers to the immune response caused by mitogen alone (such as by use of Reagent D).

EXAMPLE 5

Determination of immune reserve

PBLs from a patient with immune system deficiency due to AIDS or ARC are assayed in accordance with the foregoing procedure using Amplifier Beta. The attending physician determines that the patient's immune reserve is sufficient to make it advisable, in the physician's medical judgment, to attempt to restore it by administration of an amplifier. (For example, immune reserve above 0.5 U/ml.)

EXAMPLE 5A

Immune reserve of second patient

PBLs from a second patient with immune system deficiency due to AIDS or ARC are assayed in accordance with the same procedure. The attending physician determines that the patient's immune reserve is insufficient to make it advisable, in the physician's medical judgment, to attempt to restore it by administration of an amplifier. (For example, immune reserve below 0.1 U/ml.) No amplifier treatment is attempted.

EXAMPLE 5B

TGG immune reserve determination

Examples 5 and 5A are repeated using the TGG assay procedure instead. The results are the same.

EXAMPLE 6

Titration of amplifier dosage

The physician of Example 5 administers to the patient of Example 5 a daily dosage of Amplifier Beta of Example 7 of the '724 application equivalent to that derived from 400,000 leukocytes. After one week the physician reassays the patient's immune response in accordance with the foregoing procedure. The physician determines, in his or her medical judgment, that the base immune response has now been restored to an acceptable level. (For example, base immune response of at least 1.0 U/ml.)

Thereafter, the physician administers to the patient a weekly dosage of Amplifier Beta equivalent to that derived from 400,000 leukocytes.

At monthly intervals, the physician reassays the patient's base immune response and makes a determination whether the dose of Amplifier Beta should be increased or decreased, in order to maintain the base immune response at an acceptable level.

EXAMPLE 6A

TGG titration of amplifier dosage

The procedure of Example 6 is repeated with the assay procedure using TGG instead. The results are the same.

EXAMPLE 7

Titration of chemotherapy

PBLs from a patient undergoing chemotherapy are assayed in accordance with the foregoing procedure for Amplifier Beta. The attending physician determines that the patient's immune reserve has been lowered to a value below that which the physician, in his or her medical judgment, considers acceptable. (For example, below 0.5 U/ml.)

The physician decreases the chemotherapy dosage to 50% of its former level, or in the alternative prescribes twice-weekly dosages of Amplifier Beta (for example, each dose equivalent to material from 400,000 leukocytes). After one week the physician reassays the patient's immune response in accordance with the same procedure. The physician determines, in his or her medical judgment, that the immune reserve is now at an acceptable level. (For example, approximately 0.8 U/ml.)

At weekly intervals, the physician reassays the patient's immune response and makes a determination whether the chemotherapy dosage is at as high a level as possible without lowering the patient's maximal immune response below a level that the physician considers acceptable.

EXAMPLE 7A

TGG titration of chemotherapy

The procedure of Example 6 is repeated with the TGG assay procedure instead. The results are the same.

The foregoing assay procedure may be expanded to use in cows, pigs, and other animals, by extrapolation from the data on human beings, in a manner that will be obvious to those skilled in the art.

VI. Gamma-interferon Assay

The general IL-2 assay method described above can be modified to include any measurable lymphokine (biological response modifier). For example, gamma-interferon can also be measured on the same supernatants used for IL-2. Quantitation of gamma-interferon in such culture supernatants is advantageously accomplished by using a solid phase radioimmunoassay marketed by Centocor Inc., Malvern, Pa., which employs two monoclonal antibodies specific for gamma-interferon. Example 8 illustrates this assay using PBLs from an AIDS patient. Preparations E and F of 0.5 and 1.0 ug/ml PHA, respectively, are prepared. Preparations G, H, I, and J of sterile saline, and 1:500, 1:1000, and 1:2000 Amplifier Beta, respectively, are prepared. This permits eight tests, using E and F respectively against G, H, I, and J. A reference is established, as before.

EXAMPLE 8

Gamma-interferon assay

PBLs from an AIDS patient are prepared and the procedures of Examples 2 and 3 are repeated, with monoclonal antibody assay for gamma-interferon substituted for thymidine uptake assay for IL-2. Preparations E through J are used, the results are observed, and the results are tabulated in Table 5.

TABLE 5

| Results of Gamma-interferon Assay on Beta, PHA-stimulated AIDS patient PBLs | | |
|---|---|---|
| PHA Conc. | Beta Conc. | U/ml Gamma-interferon Prod. |
| 0.5 | control | 20 |
|  | 1:500 | 28 |
|  | 1:1000 | 30 |
|  | 1:2000 | 32 |
| 1.0 | control | 52 |
|  | 1:500 | 74 |
|  | 1:1000 | 68 |

TABLE 5-continued

| Results of Gamma-interferon Assay on Beta, PHA-stimulated AIDS patient PBLs | | |
|---|---|---|
| PHA Conc. | Beta Conc. | U/ml Gamma-interferon Prod. |
|  | 1:2000 | 82 |

It is observed that gamma-interferon production is increased by Amplifier Beta. The preceding assays are radioimmunoassays. The procedure may, if desired, be modified to ELISA assays, which involve no radioisotope and instead provide a fluorescent readout. ELISA assays are well known in the art and require no detailed description here. See, e.g., E. Leinikki et al., *ELISA Assay* of Specific Rubella Antibody Levels, 8 J. Clin. Microbiol. 419 (1979); E. Engvall and P. Perlmann, *ELISA: Quantitative Assay of Immunoglobulin,* 8 Immunochem. 871 (1971). It should be noted that an ELISA assay may be used to assay IL-2 production, also, as well as that of other lymphokines.

GENERAL CONCLUDING REMARKS

The above described procedures disclose what the inventor believes is a unique and hitherto unknown method of assaying human or animal immune system response. Although the procedure was described primarily in terms of assaying human immune system response based on T4 helper cell production of IL-2, it is believed that the procedure may be extended to measure other human and animal cell-mediated immune system functions, such as gamma-interferon, by using appropriate mitogens or antigens and appropriate indices of immune response attributable to the type of cell with regard to which the assay is conducted.

While the invention has been described in connection with a specific and preferred embodiment thereof, it will be understood that it is capable of further modifications without departing from the spirit and scope of the invention. This application is intended to cover all variations, uses, or adaptations of the invention, following, in general, the principles of the invention and including such departures from the present disclosure as come within known or customary practice within the art to which the invention pertains, or as are obvious to persons skilled in the art, at the time the departure is made.

TECHNOLOGY OF CLAIMS

As used in the following claims, the term peripheral blood lymphocyte refers to the mononuclear cell populations (PBLs) isolated as described in Example 1, supra. However, the procedure of Example 1 may be varied in ways familiar to those skilled in the art, and the reuslt will still be regarded by those skilled in the art as PBLs.

The term mitogen ordinarily means any substance capable of inducing proliferation or lymphocytes. Mitogens include, among other things, PHA, pokeweed, and tetanus toxoid. The term antigen means a defined substance, such as tetanus toxoid, that produces a specific immune response. As used in the claims, mitogen includes antigen, as well as mitogen as defined above.

The term amplifier includes TGG and its pharmaceutically acceptable salts, amides, esters, and protected derivatives thereof, as well as the immunoamplifiers described and/or claimed in the inventor's '379 patent and '724 application.

The term magnitude of effect of a dosage of a therapeutic agent refers to the amount by which the agent changes immune system response. The term direction of effect of such a dosage refers to whether the agent increases or decreases immune response. Thus an amplifier would increase immune response, so that the direction of the effect was that of increase, while a suppressor would have an effect in the opposite direction. Also, an increase in the dosage of an amplifier would ordinarily increase immune response, while a decrease in dosage of an amplifier would ordinarily have an effect in the opposite direction, i.e., to decrease immune response. (Ordinarily, that would be the effect, but there is also the paradoxical effect of high concentrations, noted above.) An increase in dosage of a chemotherapeutic agent would ordinarily decrease immune response, while a decrease of such dosage would ordinarily have an effect in the opposite direction.

The effect of amplifier on immune system response, as described in the preceding paragraph, can be represented as an increasing function within a certain range. At a certain point, however, increased dosages of amplifier decrease, rather than increase, immune response. This has been referred to earlier as the "paradoxical" effect. The first part of the range may therefore be termed the nonparadoxical dosage range, and the second part may be termed the paradoxical dosage range. The former begins at zero added amplifier and continues until the paradoxical effect sets it, whereupon the second range begins.

The term "immune reserve" is used in the claims in the sense stated supra in the Summary of the Present Invention and in the paragraph preceding Example 5.

The term "immunodeficient condition" as used in the claims includes systemic immune deficiency arising from, among other things, aging, cancer, AIDS, ARC, chemotherapy, and refractory infections. Moreover, certain apparent autoimmune conditions have immunodeficient components, as well, rheumatoid arthritis being an example. Hence, the term is intended to include such conditions, also.

What is claimed is the following:

1. A method of assaying human or animal immune system response that comprises the following steps:
   (1) Preparing a peripheral blood lymphocyte population from a blood sample taken from a human or animal subject;
   (2) Exposing a portion of said population to a mitogen and an amplifier;
   (3) Assaying the production in said population of a material that is an index of immune system response induced by said mitogen exposure.

2. The method of claim 1 wherein said subject is a human subject.

3. The method of claim 2 wherein said mitogen is PHA, pokeweed, or tetanus toxoid.

4. The method of claim 2 wherein said amplifier is Amplifier Beta.

5. The method of claim 2 wherein said amplifier is TGG.

6. The method of claim 2 wherein said material is IL-2.

7. The method of claim 6 wherein said production is assayed by measuring thymidine incorporation.

8. The method of claim 7 wherein said thymidine is radioactively tagged.

9. The method of claim 2 wherein said material is gamma-interferon.

10. The method of claim 9 wherein said production is assayed by use of at least one monoclonal antibody.

11. The method of claim 10 wherein a said antibody is radioactively tagged.

12. The method of claim 1 wherein the procedure is performed a plurality of times, successively using different concentrations of amplifier in step (2).

13. The method of claim 1 wherein, after steps 1 to 3 are performed:
   (4) a further portion of said population is assayed in accordance with the procedure of said method but with the change that the concentration of said amplifier in step (2) is reduced to approximately 0%;
   (5) the production in said population of said material is assayed as in step (3); and
   (6) the results of the assays of steps 1-3 and 4-5 are compared.

14. A method of determining an appropriate dosage of a therapeutic agent, where said agent affects cell-mediated immune system response of a human or animal subject, and where said dosage is determined to be appropriate or inappropriate by comparing the magnitude and direction of effect of said dosage on said subject's immune system response, relative to a desired or predetermined level of said effect on said subject's immune system response, said method comprising:
   (1) determining said subject's immune reserve in accordance with the method of claim 1, wherein the procedure is performed a plurality of times, successively using different concentrations of amplifier in step (2), one of said concentrations being approximately 0%, thereby producing an immune reserve assay result;
   (2) repeating the procedure of step (1) with a reference subject having said desired or predetermined level of said effect on said subject's immune system response, thereby producing a reference immune system assay result, and making a comparison of said immune reserve assay result with said reference immune system assay result;
   (3) as a result of said comparison, making a determination whether said subject's immune reserve is below, equal to, or above said level of immune system response which is desired or predetermined;
   (4) increasing, maintaining the same, or decreasing said dosage, in accordance with said determination.

15. The method of claim 14 wherein said therapeutic agent has the effect of suppressing said immune system response, and wherein, when said assay result indicates an immune reserve below that which is desired or predetermined, the dosage of said agent is decreased.

16. The method of claim 14 wherein said therapeutic agent has the effect of amplifying said immune system response, and wherein, when said assay result indicates an immune reserve below that which is desired or predetermined, the dosage of said agent is increased within the nonparadoxical dosage range.

17. The method of claim 14 wherein said therapeutic agent has the effect of amplifying said immune system response, and wherein, when said assay result indicates an immune reserve above that which is desired or predetermined, the dosage of said agent is decreased.

18. The method of claim 16 wherein the subject is a human subject, the therapeutic agent is an amplifier, and the subject suffers from an immunodeficient condition.

19. The method of claim 16 wherein the assay is based on mitogen-based production of IL-2.

20. The method of claim 16 wherein the assay is based on mitogen-induced production of gamma-interferon.

21. The method of claim 16 wherein the assay is an ELISA assay.

22. A method of assaying the immune system response of a human test subject that comprises the following steps:
(1) Preparing a peripheral blood lymphocyte population from a blood sample taken from said subject;
(2) Exposing a portion of said population to a mitogen and an amplifier;
(3) Assaying the production in said population of IL-2, by measuring the uptake of radioactively tagged thymidine, whereby an assay result is produced; and
(4) repeating steps 2 and 3 at least one more time with a different concentration of amplifier in step 2.

23. The method of claim 22 adapted to the titration of amplifier dosage being administered to a test subject who has an immunodeficient condition, wherein the maximum assay result of the procedures described in said method is compared with a predetermined reference immune system assay result, and wherein
if said maximum assay result exceeds said reference assay result, said amplifier dosage is decreased, and
if said reference assay result exceeds said maximum assay result, said amplifier dosage is increased.

24. The method of claim 22 adapted to the determination whether a test subject with an immunodeficient condition has sufficient immune reserve to warrant treatment of the subject with an amplifier, wherein the maximum assay result of the procedures described in said method is compared with a predetermined reference immune system assay result, and wherein
if said maximum assay result exceeds said reference assay result, said subject is treated with amplifier, and
if said reference assay result exceeds said maximum assay result, said subject is not treated with amplifier.

25. The method of claim 24 wherein the immunodeficient condition is AIDS or ARC.

* * * * *